US006930775B1

(12) United States Patent
Spremo et al.

(10) Patent No.: US 6,930,775 B1
(45) Date of Patent: Aug. 16, 2005

(54) DIFFRACTION-BASED OPTICAL CORRELATOR

(75) Inventors: Stevan M. Spremo, Campbell, CA (US); Peter L. Fuhr, Santa Cruz, CA (US); John F. Schipper, Palo Alto, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 314 days.

(21) Appl. No.: 10/303,172

(22) Filed: Nov. 22, 2002

(51) Int. Cl.[7] .............................................. G01J 3/28
(52) U.S. Cl. ................................... 356/328; 435/288.7
(58) Field of Search .............................. 356/328, 334; 436/2, 171; 435/2, 288.7

(56) References Cited

U.S. PATENT DOCUMENTS

| | | | |
|---|---|---|---|
| 3,924,949 A * | 12/1975 | Honkawa et al. ........... 356/320 |
| 4,833,637 A | 5/1989 | Casasent et al. |
| 4,983,039 A * | 1/1991 | Harada et al. .............. 356/328 |
| 5,444,528 A | 8/1995 | Puschell |
| 5,615,008 A * | 3/1997 | Stachelek ................... 356/301 |
| 5,671,090 A | 9/1997 | Pernick et al. |
| 5,814,820 A | 9/1998 | Dong et al. |
| 5,905,571 A | 5/1999 | Butler et al. |
| 6,204,926 B1 | 3/2001 | Maznev et al. |
| 6,608,678 B1 * | 8/2003 | Potyrailo et al. ........... 356/301 |

* cited by examiner

Primary Examiner—F. L. Evans
Assistant Examiner—Kara Geisel
(74) Attorney, Agent, or Firm—John F. Schipper; Robert M. Padilla

(57) ABSTRACT

Method and system for wavelength-based processing of a light beam. A light beam, produced at a chemical or physical reaction site and having at least first and second wavelengths, $\lambda 1$ and $\lambda 2$, is received and diffracted at a first diffraction grating to provide first and second diffracted beams, which are received and analyzed in terms of wavelength and/or time at two spaced apart light detectors. In a second embodiment, light from first and second sources is diffracted and compared in terms of wavelength and/or time to determine if the two beams arise from the same source. In a third embodiment, a light beam is split and diffracted and passed through first and second environments to study differential effects. In a fourth embodiment, diffracted light beam components, having first and second wavelengths, are received sequentially at a reaction site to determine whether a specified reaction is promoted, based on order of receipt of the beams. In a fifth embodiment, a cylindrically shaped diffraction grating (uniform or chirped) is rotated and translated to provide a sequence of diffracted beams with different wavelengths. In a sixth embodiment, incident light, representing one or more symbols, is successively diffracted from first and second diffraction gratings and is received at different light detectors, depending upon the wavelengths present in the incident light.

50 Claims, 7 Drawing Sheets

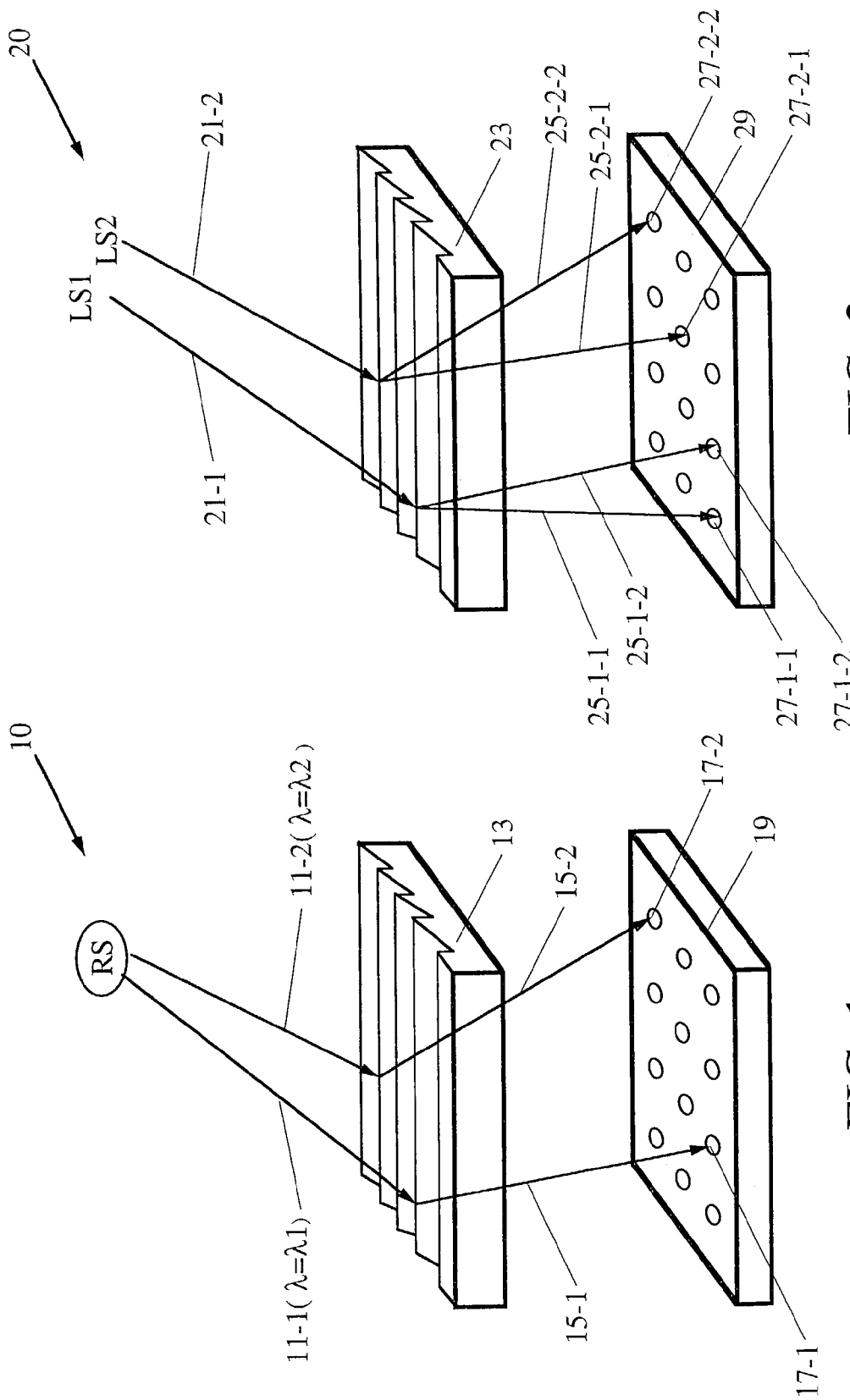

DIFFRACTION-BASED OPTICAL CORRELATOR

FIELD OF THE INVENTION

This invention relates to multi-dimensional control of direction of a light beam, using diffraction, to study certain wavelength effects.

BACKGROUND OF THE INVENTION

In certain applications involving chemical and/or physical reactions, presence of light having any of a specified set of wavelengths will cause the reaction to proceed, whereas absence of all of this specified set of wavelengths will either suppress the reaction or will cause the reaction to proceed at a markedly lower rate or to fail to go to completion. In some situations, it is desirable to determine which of two or more groups of wavelengths within the specified set was present, if the reaction proceeds, to correlate the wavelengths present with an observed reaction rate or for some other purpose. In other situations, it is desirable to provide separate groups of non-overlapping wavelengths and to monitor the reaction simultaneously or sequentially for reaction rate and/or completion of the reaction.

What is needed is a system that provides N-dimensional control (with N=2 or 3) of direction of propagation of a light beam, that varies this direction according to a representative wavelength of the light beam, and that provides simultaneous separation of the light beam into different wavelength groups that are directed to different detectors or reaction sites. Preferably, the system should provide a light beam propagation direction that varies monotonically with wavelength in a selected wavelength interval.

SUMMARY OF THE INVENTION

These needs are met by the invention, which provides a system including one, two or more diffraction gratings, positioned in a selected configuration so that an initial light beam having a representative wavelength $\lambda$ is received and diffracted by a first grating having a first orientation, to produce a first beam having a first propagation direction determined by $\lambda$. Optionally, the first beam is received and diffracted by a second grating having a second orientation, to produce a second beam having a second propagation direction that is also determined by $\lambda$, where the second grating orientation is approximately perpendicular or transverse to the first grating orientation. The resulting beam propagation direction varies with $\lambda$ in such a manner that, within a selected wavelength interval $\lambda 1 \leq \lambda \leq \lambda 2$, no two initial light beams having respective representative wavelengths, $\lambda'$ and $\lambda''$ with $|\lambda'-\lambda''|$ greater than a threshold difference $\Delta\lambda(thr)$, will produce resulting light beams having the same beam propagation direction; and a difference in propagation directions for these two resulting beams will increase (preferably monotonically) with the wavelength difference $|\lambda'-\lambda''|$.

In a first embodiment, light produced at a reaction site is received by the diffraction system, and resulting beams for each of two or more different wavelength groups are directed to two or more light detector elements in a detector array to monitor production of light in different wavelengths groups and at different times during and following the reaction. In a second embodiment, first and second light beams are sampled at a sequence of times and are compared at two or more wavelengths to determine if the beams are received from the same light source or from different light sources, using correlation techniques. Alternatively, one of the light beams (e.g., the first) is replaced by data from a (virtual) reference beam, and characteristics of the remaining light beam are compared with those of the reference beam, using correlation techniques.

In a third embodiment, first and second chambers, containing a control or reference medium and an altered medium, respectively, are positioned in first and second paths of light beams that have been diffracted by one or two gratings and that have the same group of wavelength ranges. Where two diffraction gratings are used, the same wavelength range for each of the first and second light beams can be received and compared for-amplitude contrast analysis, phase contrast analysis, or chamber medium comparison at the same light detector in the array, or at different detectors. Where one diffraction grating is used, the first and second light beam components having the same wavelength range are received at different light detector elements, and the signals are combined electronically.

In a fourth embodiment, each of two or more detector elements is replaced by a reaction site, and the effectiveness of incident light in each of two or more wavelength groups, in promoting a given reaction, is monitored at the detector array.

In a fifth embodiment, a diffraction grating is provided on the surface of a first cylinder. A second, coaxial cylinder, having a larger diameter than the first cylinder, has an array of light detectors that receive light beams in various wavelength ranges that have been diffracted by the grating. One or both of the first cylinder and the second cylinder can rotate or be translated axially relative to the other cylinder to monitor receipt of different wavelength ranges. Any of the gratings used in these embodiments can be chirped or conventional.

BRIEF DESCRIPTION OF THE DRAWINGS

FIGS. 1, 2, 3, 4 and 9 illustrate five embodiments of the invention that may rely upon correlation of corresponding wavelength components for two signals.

DESCRIPTION OF BEST MODES OF THE INVENTION

Figure 3:
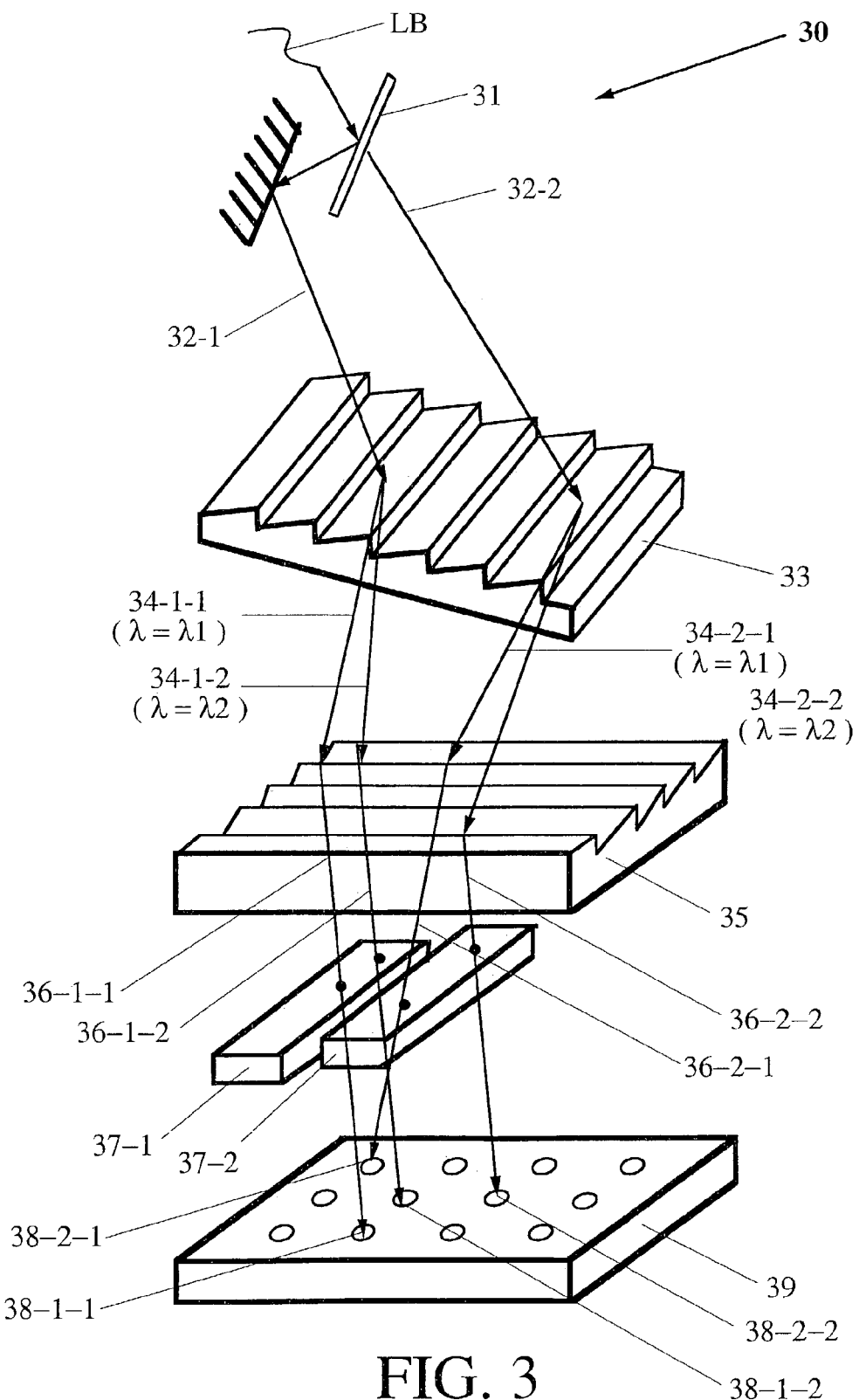

In a first embodiment 10, illustrated in FIG. 1, an incident light beam, having two or more spaced apart wavelengths, $\lambda 1$ and $\lambda 2$, may arise from light emitted at a reaction site RS as a result of a chemical or physical reaction, such as fluorescent light or phosphorescent light produced as a time delayed response to an atomic or molecular rearrangement of one or more atomic or molecular constituents at the reaction site. Beam components, 11-1 ($\lambda=\lambda 1$) and 11-2 ($\lambda=\lambda 2$), corresponding to the different wavelengths are received and diffracted in different directions at a diffraction grating 13, producing corresponding diffracted beams, 15-1 and 15-2, which are received at two light detectors, 17-1 and 17-2, respectively, that are part of a detector array 19. Optionally, each detector, 17-1 and 17-2, has a timing mechanism that determines a time interval, if any, at which light in a corresponding (non-overlapping) wavelength interval is received at the detector for a corresponding wavelength group, λ=λj (j=1, 2). This embodiment allows monitoring of wavelength production, and of the time interval of wavelength production, of light in each wavelength group (λj) at the reaction site RS. This embodiment can be extended to more than two wavelength groups (λj). The light detector array 19 can be linear or curvilinear, in one or two dimensions.

In an embodiment 20 illustrated in FIG. 2, first and second light beams, 21-$h$ (h=1, 2), not necessarily from the same source, are received and diffracted at a grating 23 from different orientations. Each light beam, 21-1 and 21-2, has two or more spaced apart wavelength groups (λ≈λj; j=1, 2, . . . ). First and second diffracted light beam groups, 25-1-$j$ and 25-2-$j$, produced at the grating 23 are received and analyzed at corresponding light detectors, 27-1-$j$ and 25-2$j$) in an array 29 of light detectors. The detector array 29 may be linear or curvilinear, in one or two dimensions. Optionally, each light detector 27-$h$-$j$ (h=1, 2; j=1, 2, . . . ) has a timing mechanism that samples the input signal wavelength group (λj) at each of the detectors 27-$h$-$j$ at a specified sequence of time points, t=$t_{k,j,h}$(k= 1, 2, . . . K), and records and stores an input signal value s(τ+$t_{k,j}$;λj,h) for light beam number h (h=1, 2). Alternatively, one of the input signal value sequences s(τ+$t_{k,j}$;λj;h=2) can be replaced by a reference signal value sequence s(τ+$t_{k,j}$;λj;ref) for a (virtual) reference light beam so that only one light beam 21-1 is received and diffracted by the grating 23. The system then receives a measured or observed input light beam 21-1 from what is postulated to be the same light source, processes the different wavelength components (λj) for the observed beam, and again samples the observed input signal values s(Δt+$t_{k,j}$;λj;h=1), where Δt is a fixed but arbitrary time value, and temporarily holds these values. The analysis module 29 forms a set of correlation functions $$C(\tau 1, \tau 2; \lambda j) = \sum_{k=1}^{K} s(\tau 1 + t_{k,j}; \lambda j; 1) \cdot s(\tau 2 + t_{k,j}; \lambda j; 2), \quad (1)$$

and varies the time shift difference, τ1−τ2, (using linear or quadratic or polynomial interpolation, as appropriate) to obtain a maximum amplitude, denoted C(τ1; τ2; λj; max, for the quantity in Eq. (3) for each of the wavelength groups (λj) (j= 1, . . . , J). The time shift difference τ1−τ2, may depend upon the index j. Ideally, the time shift difference is independent of j. The analysis module 29 now forms a weighted sum $$C(\max) = \sum_{j=1}^{J} w_j \cdot C(\tau 1; \tau 2; \lambda j; \max), \quad (2)$$

$$\sum_{j=1}^{J} w_j = 1 \; (w_j \geq 0), \quad (3)$$

and compares the weighted sum C(max) with a threshold number C(thr), defined as $$C(thr) = \sum_{j=1}^{J} w_j \sum_{k=1}^{K} |s(t_{k,j}; j; ref)|^2. \quad (4)$$

If C(max)≧f·C(thr), where f is a selected fraction (0<f<1), the analysis module 39 interprets this condition as indicating that the source of the observed light beam 31-obs is the same as the reference light source.

If C(max)<f·C(thr), the analysis module 29 interprets this result as indicating one of several conditions: (1) the observed light beam source is not the reference light beam source; (2) the observed light beam source is related to, but qualitatively different from, the reference light beam source; and (3) the observed light beam source is substantially the same as the reference light beam source but has changed with the passage of time.

If C(max) is less than but close to f·C(thr), the possibility that condition (3) is present is investigated, for example, by recomputing C(t1,t2;j;max) for each of a sequence of increasing values of the time difference |τ1−τ2|. If C(τ1; τ2; λj; max) is monotonically decreasing, or approximately so, with increasing values of |τ1−τ2|, it is likely, although not guaranteed, that condition (3) is present. Condition (3) may be present if the reference light beam source is aging or otherwise drifting with the passage of time. If C(max) is substantially lower than C(thr) (e.g., C(max)≦0.5·C(thr)), it is more likely that the observed light beam source is different from the reference light bean source (condition (1)).

In another embodiment 30, illustrated in FIG. 3, an initial light beam LB produced by a light source is received by a light beam splitter 31 and split into substantially identical first and second light beams, 32-$h$ (h=1, 2). The first and second light beams, 32-1 and 32-2, are received and diffracted by a first diffraction grating 33 to produce diffracted beams 34-1-$j$ and 34-2-$j$ centered at spaced apart wavelength groups, λ=λj(j=1, 2, . . . ). Optionally, the diffracted beams 34-$h$-$j$ are received and diffracted again by a second diffraction grating 35. The corresponding diffracted beams 36-$h$-$j$ pass through a first light beam interrogation chamber 37-1 (h=1) or through a second light beam interrogation chamber 37-2 (h=2) and are received at light detectors 38-$h$-$j$ that are part of an array 39 of detectors.

The first and second light beam interrogation chambers, 37-1 and 37-2, are positioned to receive the diffracted first and second light beams and to allow the diffracted light beams to interact with the contents of the respective first and second chambers. It is assumed that the light beam input and output interfaces of the two interrogation chambers are substantially the same for each wavelength range (λj). The first and second interrogation chambers, 37-1 and 37-2, can be positioned (1) between the beam splitter 31 and the first grating 33, (2) between the first grating 33 and the second grating 35, (3) between the second grating 35 and the array 39 of light detectors 38-$h$-$j$, or (4) to include one or both of the gratings, 33 and 35. In some situations, the second grating 35 may be deleted, and the first grating 33 may provide sufficient wavelength spreading to allow receipt of the once-diffracted beams 34-$h$-$j$ at different light detector elements 38-$h$-$j$ (h=1, 2; j=1, 2, . . . ). The first and second light beams have the same initial characteristics and preferably arise from the same source, but at least one of the environments (interrogation chambers) through which the first and second beams pass may change.

Assume that each of the light beams, 36-*h-j* travels an optical path length d (or d(λ)) within the corresponding interrogation chamber, 37-1 and 37-2. The distance d may correspond to a single pass, or to many repeated passes, through each chamber. With the interrogation chamber 37-1 in a reference condition (e.g., ambient medium either absent or unperturbed), each of the detectors 38-*h-j* (h=1) receives and records a wavelength-dependent signal s(t+τ+$t_{k,j,h=1}$;j; h=1), where the index j refers to a central wavelength, λ=λj of the jth wavelength component. The interrogation chamber 37-2 corresponds to a non-reference or perturbed or altered environment that is to be monitored, and two or more diffracted beams from the second light beam 32-2, having the same initial characteristics as the first light beam 32-1, are sent through different paths in the system shown in FIG. 3. Signals s(t+τ+$t_{k,j,h=2}$;j;h=2) are received and recorded at the detector elements 38-*h-j* (h=2), and the signals s(t+τ+$t_{k,j,h}$;j;h) (h=1 and 2) are compared and analyzed by the detector-analyzer module 39 in order to characterize the non-reference environment in the interrogation chamber 37-2.

In many situations, the second diffraction grating 35 can be deleted so that a single diffraction grating 33 is used. In these situations, the once-diffracted light beams, 34-1-1 and 34-1-2, are received directly by, and pass through, the first interrogation chamber 37-1, and the once-diffracted light beams, 34-2-1 and 34-2-2, are directly received by, and pass through, the second interrogation chamber 37-2. This simplifies the system but may impose some constraints on the locations of the corresponding light detectors, 38-1-1, 38-1-2, 38-2-1 and 38-2-2.

In amplitude contrast signal processing, for a particular wavelength range (λj), the multiplicative attenuation component for the reference environment and the non-reference environment may be approximately characterized by exponential attenuation functions, exp{−μ(λj; 1)·d} and exp{−μ(λj;2)·d}, where μ is an absorption and scattering coefficient and the optical path distance d may correspond to a single pass or to many passes through each of the chambers 37-1 and 37-2. The reference attenuation coefficient exp{−μ(λj; 1)·d} may have the value 1, corresponding to μ(λj; 1)≈0, if the reference environment within the chamber 37-1 is substantially a vacuum. The difference of the two signals received at the light detector element 38-*j* will be proportional to $$\Delta 1(\lambda j) = \exp\{-\mu(\lambda j; 1)\cdot d\} - \exp\{-\mu(\lambda j; 2)\cdot d\}, \quad (5A)$$

and this difference can be used to characterize the non reference environment for the wavelength component λj (j=1,2, ..., J) in the chamber 37-2. A ratio of the two signals received at the light detector element (λj) will be proportional to $$\Delta 2(\lambda j) = \exp\{-\{\mu(\lambda j);1) - \mu(\lambda j;2)\}\cdot d\} \quad (5B)$$

Either or both of these measurements can be processed and analyzed to characterize the light beam propagation path. The altered environment sensed in the interrogation chamber 37-2 may involve a change in temperature, in partial pressure, in relative concentration of one, two or more fluid species and/or in another physical or chemical parameter of interest.

Alternatively, first and second interrogation chambers, 37-1 and 37-2, are positioned in the light beam propagation paths of the respective wavelengths λ1 and λ2, between the grating 33 and the detector-analyzer module 39, or in a combination of these con figurations, with or without presence of the first interrogation chamber 37-1. Optionally, the first and second interrogation chambers, 37-1 and 37-2, are spaced apart laterally so that a diffracted light beam component with a given wavelength λ does not pass through both the first chamber 37-1 and the second chamber 37-2.

Preferably, the optical path lengths in the first interrogation chamber 37-1 of the first wavelength components of the first and second diffracted beams are substantially the same. Preferably, the optical path lengths in the second interrogation chamber 37-2 of the second wavelength components of the first and second diffracted beams are also substantially the same.

Juxtaposition of signals received after-passage of the diffracted first and second light beams through the respective first and second interrogation chambers, 37-1 and 37-2, may also be analyzed using phase contrast signal processing (rather than amplitude contrast signal processing), in which a phase difference Δφ(x,y) occurs between the light beam paths passing through the first and second chambers, 37-1 and 37-2, irrespective of whether or not an (substantial) amplitude difference occurs. Phase contrast analysis is briefly discussed in M. Born and E. Wolf, *Principles of Optics*, Pergamon Press, Oxford, Fifth Edition, 1975, pp. 421–428, and E. Hecht, *Optics*, Addison Wesley, Third Edition, 1998, pp. 611–618. In this approach, a sequence of light beamlets, having each of the wavelength ranges λj of interest, preferably passes through each of the two chambers, 37-1 and 37-2, so that a phase contrast or comparison can be made for each of these wavelength ranges.

In a simplified analysis, where a resulting phase difference Δφ=Δφ(x,y;λj) for a (wavelength-dependent) path through each of the first and second interrogation chambers, 37-1 and 37-2, is a very small fraction of a quarter cycle (|Δφ|<<π/2) and does not vary rapidly with the location coordinates (x,y), a signal difference component Δs(1,2;x,y;λj) between signals received along two corresponding paths (having the same wavelength range but passing through different chambers) may be characterized as $$\Delta s(1, 2; x, y; \lambda j) = A(j)\{\sin(\omega(j)t) - \sin(\omega(j)t + \Delta\phi)\} \quad (6)$$

$$= A(j)\{\{1 - \cos(\Delta\phi)\} - \sin\omega(j)t - \cos(\omega(j)t)\cdot\sin(\Delta\phi)\}$$

$$\approx -A(j)\cdot\cos(\omega(j)t)\cdot\sin(\Delta\phi),$$

where A(j) is an amplitude associated with the wavelength range λj, ω(j)= 2πc/(η(λj)·λj), and η(λj) is a refractive index of the ambient medium for the wavelength range λj). The summation operation indicated in Eq. (6) may be replaced by a combination of a summation operation and an integration operation, in appropriate circumstances. By arranging for different wavelength ranges λj to be received at different detectors 38-*h-j* at the analysis module 49 in FIG. 3, the phase difference can be characterized for each of these wavelength ranges, and a collective picture of phase difference of the two signal paths can be computed:

$$\Delta s(1,2;x,y) \approx -\Sigma_j A(j)\cdot\cos(\omega(j)t)\cdot\sin(\Delta\phi(x,y;\lambda j)). \quad (7)$$

Figure 4:
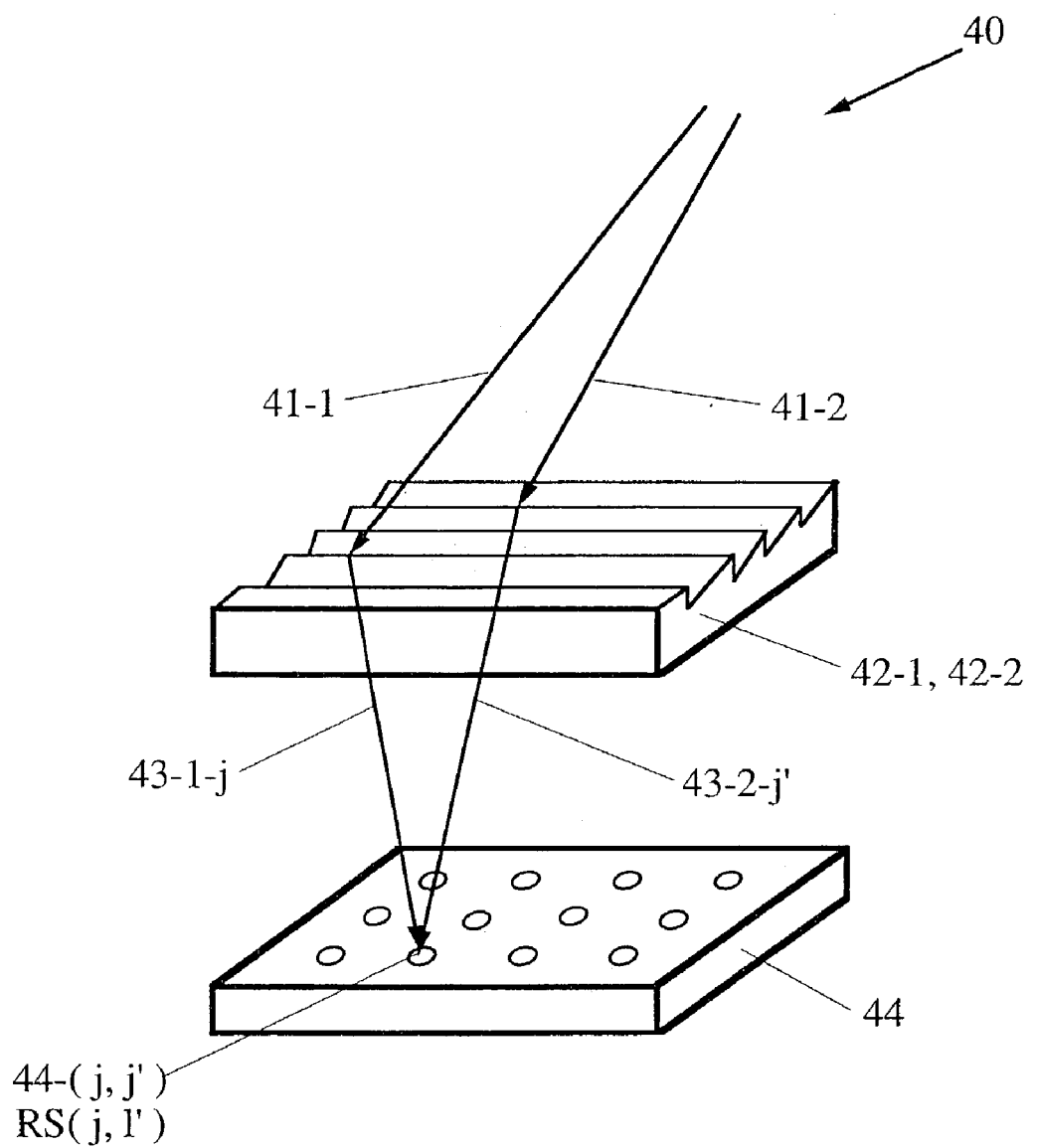

FIG. 4 illustrates an embodiment 40 where first and second light beams, 41-1 and 41-2, preferably from different sources, are received at a first diffraction grating 42-1 (or at first and second diffraction gratings, 42-1 and 42-2, respectively). Diffracted beams, 43-1-*j* and 43-2-*j'* (corresponding to wavelengths λ=λj and λ= λj', respectively) are then received at a reaction site RS(j,j') and an associated chemical state detector 44. Receipt of the diffracted beams, 43-1-$j$ and 43-2-$j'$, in that order in time, and within a specified time interval length $\Delta(j,j')$ of each other, will produce a specified reaction. In the specified reaction, the state of an initial substance will change from A0 to A(1;j) (upon absorption of light with a specified wavelength $\lambda=\lambda j$), and will change from A(1;j) to A(2;j') (upon absorption of light with a specified wavelength $\lambda=\lambda j'$). Receipt of each of the two (or more) diffracted light beams, 43-1-$j$ and 43-2-$j'$, in a particular temporal order, is necessary to promote a specific reaction at the reaction site RS(j,j'). Optionally, the diffracted light beam component 43-2-$j'$ is received at the reaction site RS(j,j') with a selected time delay, $\Delta t = \Delta t_{2,1}$ relative to the time of receipt of the diffracted light beam component 43-1-$j$ If one or both of the two diffracted light beams, 43-1-$j$ and 43-2-$j'$, is not received at the reaction site RS(j,j'), the desired reaction will not occur at that site. A sequence of spaced apart reaction sites RS(j,j') can be provided at the chemical state detector 44, with each reaction site being activated by the same pair ($\lambda j, \lambda j'$) or by a different pair of wavelengths provided by the incident light beams, 41-1 and 41-2, and the diffraction grating 42-1 (or 42-1 and 42-2).

Figure 5:
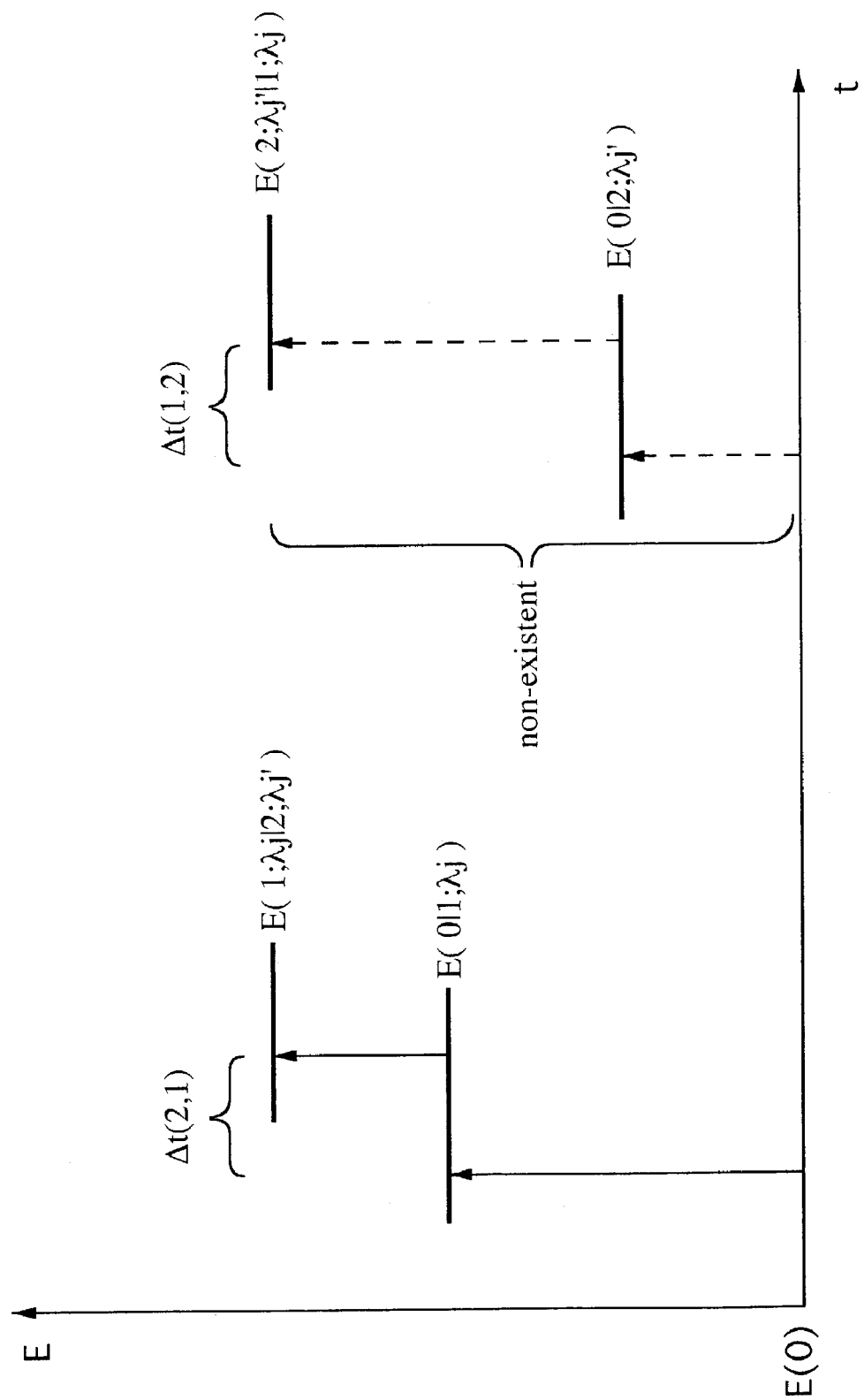
FIG. 5 graphically illustrates operation of the fourth embodiment.

Alternatively, if the two diffracted light beams, 43-1-$j$ and 43-2-$j'$, are received in the wrong order or within time intervals that are wrong relative to each other, the desired reaction will not occur. As an example of this situation, assume that receipt of the first diffracted light beam 43-1-$j$ at the reaction site at a first time, t=t1, will promote a bound electron in at least one atom or molecule from an initial state to a first excited state E(0|1;$\lambda$j), as illustrated graphically in FIG. 5; and assume that receipt of the second diffracted light beam 43-2-$j'$ at the reaction site at a second time, t=t2, will promote a bound electron in the at least one atom or molecule from an already-occupied first-excited state E(0|1; $\lambda$j) to a second excited state, denoted as an ordered excited state pair E(1;$\lambda$j|2;$\lambda$j'), that can be monitored as part of a reaction.

Receipt of the second diffracted light beam 43-2-$j'$, followed by receipt of the first diffracted light beam 43-1-$j$, at the reaction site RS(j,j') produces no substantial reaction, because (1) an excited state E(0|2;$\lambda$2) relative to the initial state does not exist and/or (2) an excited state E(2,$\lambda$j'|1;$\lambda$j) that can be reached from the excited state E(0|2;$\lambda$) (if it did exist) is not available. That is, the order of spectroscopic excitation in the atom or molecule is not commutative. This non-commutativity may arise because of the quantum selection rules for the target atom or molecule.

Absence of the ordered excited state pair E(2;$\lambda$j'|1;$\lambda$j) may indicate that (1) at least one of the two diffracted light beams, 43-1-$j$ and 43-2-$j'$, is absent at the reaction site or (2) the two diffracted light beams, 43-1-$j$ and 43-2-$j'$, arrive in the wrong temporal order at the reaction site or (3) the temporal separation in arrival of the first diffracted beam 43-1-$j$ before arrival of the second diffracted beam 43-2-$j'$ is not an time interval difference that is appropriate for promotion of the desired reaction.

Proceeding in this manner, the character of diffracted light received from the grating 42-1 (or 42-1 and 42-2) at the reaction site RS(j,j') can be analyzed.

Where no excited state pair E(2;$\lambda$j'|1;$\lambda$j) occurs, one can delay the first time of arrival, t=t1, by a variable amount relative to the second time of arrival, t=t2, and determine if the excited state pair E(2;$\lambda$j'|1;$\lambda$j) appears for a particular range of this first time delay. Alternatively, one can delay the second time of arrival, t=t2, by a variable amount relative to the first time of arrival, t=t1, and determine if the excited state pair E(2;$\lambda$j'|1;$\lambda$j) appears for a particular range of this second time delay.

A conventional grating has grating r/t components with uniform width d. Consider a polynomially stepped, "chirped" grating, for which the grating r/t component widths, $d = d_n$, (n=1, 2, ..., N) vary according to the index n, for example, as a polynomial in the index: $d_n = p(n)$, where p(n) is a polynomial with selected coefficients. For example, a polynomially chirped grating, oriented in the x-direction, with the nth r/t component widths given by $$d_n = p(n) = p_0 + p_1 \cdot n + p_2 \cdot n^2 + p_3 \cdot n^3, \tag{8}$$

where the coefficients $p_k$ are constant, will have r/t component centers, measured from a left edge or from a right edge of the grating, located at $$x = c_n = p_0 \cdot (n - 1/2) + p_1 \cdot n^2/2 + p_2 \cdot n(2n^2 + 1)/6 + p_3 \cdot (n^4 + n^2)/4 \quad (9)$$
$$= -p_0/2 + (p_0 + p_2/6) \cdot n + (p_1/2 + p_3/4) \cdot n^2 +$$
$$(p_2/3) \cdot n^3 + (p_3/4) \cdot n^4.$$

A conventional grating with uniform r/t component widths corresponds to $p_1 = p_2 = p_3 = 0$.

Figure 6:
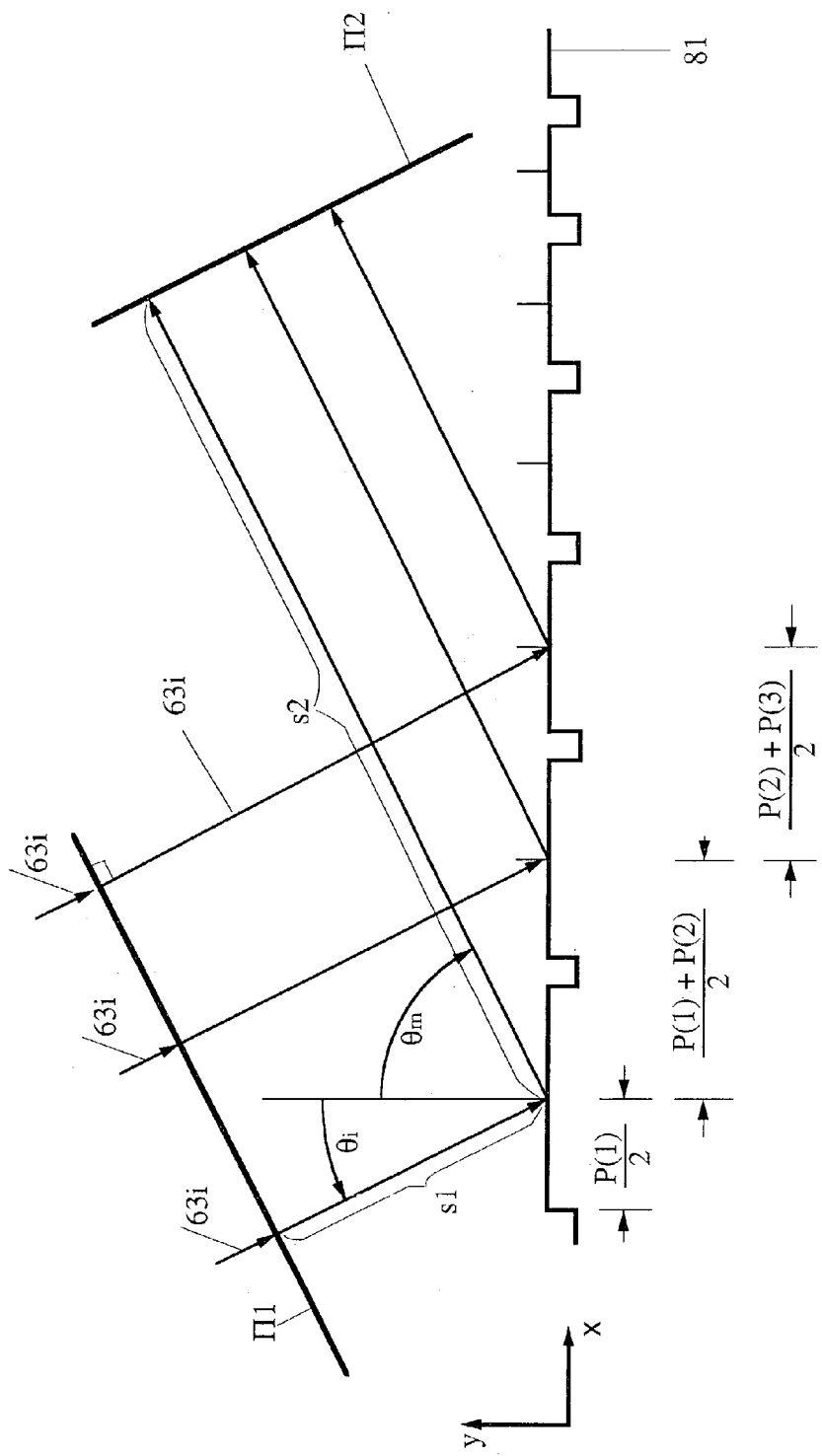
FIG. 6 illustrates response of a chirped grating.

FIG. 6 illustrates (reflective) diffraction of a light beam 63$i$ at a chirped grating 61, with an incidence angle $\theta i$ and a diffraction angle $\theta m$ corresponding to a diffraction order m and a diffracted wavelength $\lambda = \lambda_m$. The light beam diameter must permit the beam to illuminate several grating r/t components (preferably, at least 4–10) at the same time. In the xy-plane shown in FIG. 6, a first plane $\Pi 1$ of wavefronts of the incident light beam is diffracted at a grating 61 and interferes constructively at a second plane $\Pi 2$. The first and second planes, $\Pi 1$ and $\Pi 2$, are defined by the respective equations in the xy-plane $$\Pi 1: y = H1(x) = (x - x1') \cdot \tan \theta i, \tag{10A}$$

$$\Pi 2: y = H2(x) = (x2' - x) \cdot \tan \theta m \tag{10B}$$

An incident light beam ray 63$i$ is moves through the plane $\Pi 1$, and a portion thereof is received at or near the center of one of the grating r/t components (no. n), with center location $x = cn$ given in Eq. (9). The total wave is diffracted and is received at the plane $\Pi 2$. The total distance traveled by this ray in moving from the plane $\Pi 1$ to the grating r/t component (no. n) to the plane $\Pi 2$ is $$\Delta s = s1 + s2 = (c_n - x1') \sin \theta i = (x2' - c_n) \sin \theta m. \tag{11}$$

For each integer index value n the equality $$\Delta s = M \cdot \lambda / \eta(\lambda) \tag{12}$$

is preferably satisfied to provide constructive interference at the plane $\Pi 2$, where M is an integer corresponding to diffraction order, $\lambda$ is a representative wavelength of the ray and $\eta(\lambda)$ is the refractive index of the ambient medium at that wavelength.

Where the center-to-center distance, $\Delta c_n = c_{n+1} - c_n$, between adjacent r/t components is constant (independent of the integer n), corresponding to a conventional grating with uniform width r/t components, an altered form of the conventional grating equation, $$(p_0 - 2 \cdot x1') \sin \theta i + (2 \cdot x2' - p_0) \sin \theta m = 2M \cdot \lambda / \eta(\lambda), \tag{13}$$

is recovered, where the x'1 and x'2 terms are arbitrary and can be ignored.

Where the r/t component widths are given by $p(n)=p0+p1 \cdot n+p2 \cdot n^2+p_3 \cdot n^3$, corresponding to a cubically stepped, chirped grating, the basic grating equation becomes $$\{p_0/2 + (p_0 + p_2/6) \cdot n + (p_1/2 + p_3/4) \cdot n^2 + \qquad (14)$$
$$(p_2/3) \cdot n^3 + (p_3/4) \cdot n^4\}(\sin\theta i - \sin\theta m) -$$
$$x'1 \cdot \sin\theta i + x'2 \cdot \sin\theta m = M \cdot \lambda/\eta(\lambda).$$

Ideally, this is true for every integer $n=1, 2, \ldots, N$, and terms involving different powers of n can be collected and combined. This requires that $$p0 \cdot (\sin \theta i - \sin \theta m) = 2M0 \cdot \lambda/\eta, \qquad (15\text{-}0)$$

$$n \cdot (p_0+p_2/6) \cdot (\sin \theta i - \sin \theta m) = M1 \cdot \lambda/\eta, \qquad (15\text{-}1)$$

$$n^2 \cdot (p_1/2+p_3/4) \cdot (\sin \theta i - \sin \theta m) = M2 \cdot \lambda/\eta, \qquad (15\text{-}2)$$

$$n^3 \cdot (p_2/3) \cdot (\sin \theta i - \sin \theta m) = M3 \cdot \lambda/\eta, \qquad (15\text{-}3)$$

$$n^4 \cdot (p_3/4) \cdot (\sin \theta i - \sin \theta m) = M4 \cdot \lambda/\eta, \qquad (15\text{-}4)$$

where M0, M1, M2, M3 and M4 are appropriate integers, corresponding to the particular integer n, and $\lambda$ and $\eta(\lambda)$ are assumed fixed. Equations (15-0) through (15-4) are linear in the coefficients p0, p1, p2 and p3 and can be sequentially solved for these quantities. However, these relations involve five equations for four unknowns and, thus, may be over-prescribed. Over-prescription may be present for any polynomial of degree at least equal to 1. Possibly, no more than four of the five relations (15-j) (j=0–4) can be satisfied simultaneously. If Eqs. (15-0) through (15-4), which are analogous to constructive interference relations for a uniform width grating, are not all satisfied, some destructive interference may be present in the diffracted light beam that arrives at the plane Π2, resulting in a light beam intensity that is substantially less than the theoretical maximum (and probably unattainable) light beam intensity for that plane.

One interpretation here is that diffracted beamlets from less than all of the r/t components contribute to diffraction of a particular diffraction order, when a polynomially chirped grating is used. In this instance, it is usually preferable to satisfy the lower order relations, (15-0) through (15-3). The optical intensity of a particular diffraction order for a chirped diffraction grating is likely to be less than the corresponding optical intensity for a conventional grating, because not all r/t components contribute to this diffraction order. As the grating 61 and incident beam 63i are translated relative to each other, the particular r/t components that contribute to a particular grating order can change so that one or more of the diffraction angle, the order and the wavelength can change in the defining grating equation(s). One effect of this is that, as the grating 61 and incident beam 63i are translated relative to each other by a distance Δx, the observed dominant diffraction orders and the distance Δx correspond to each other in a 1-1 manner.

Figures 7, 8:
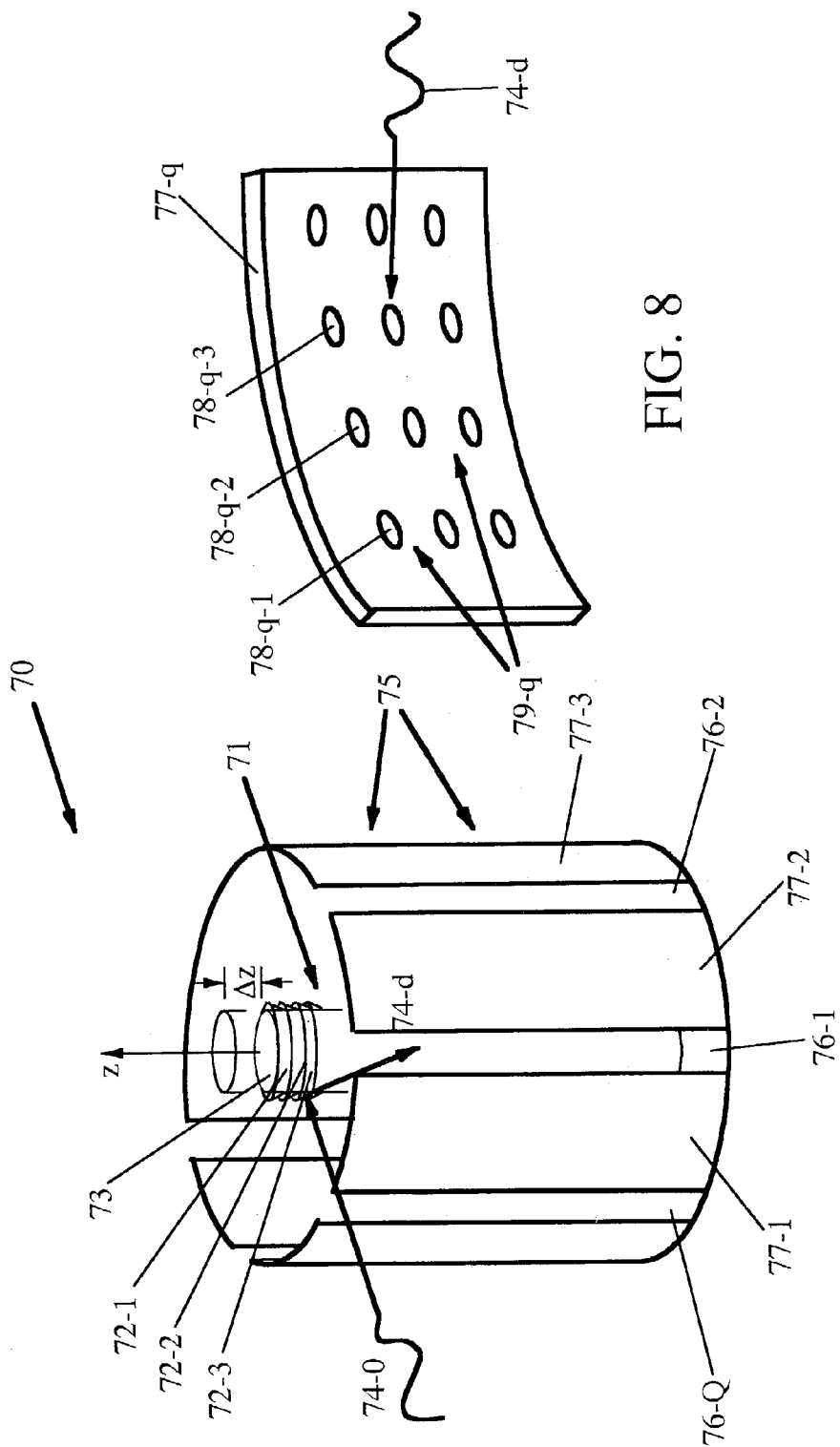
FIGS. 7 and 8 illustrate an embodiment that uses a cylindrical grating, surrounded by light detectors.

FIG. 7 illustrates another embodiment 70 of the invention, which uses a diffraction grating 71 on an inner surface of a cylinder (preferably cylindrically symmetric), to provide optical correlation information for a light beam. The grating 71 includes three or more blazed r/t components 72-$h$ (h=1, . . . , J; J≧3) positioned at the circumference of a cylinder 73 and positioned to receive an incident light beam 74-0 and to provide a resulting diffracted light beam 74-$d$. The light beam has two or more spaced apart wavelength components, Δ1, Δ2, . . . , that are to be sensed and discriminated between by the grating 71. The grating 71 is optionally chirped so that the r/t component widths $a_i$ (i=1, 2, . . . , I) are not necessarily uniform and optionally vary from one component to the next. The grating 71 can be translated a selected amount Δz along the z-axis of the cylinder 73. If the grating 71 is chirped, the portion of the grating presented to the incident light beam 74-0 can vary with the translation distance, because of the chirping. As the translation distance Δz varies, different wavelengths present in the diffracted beam 74-$d$ will be emphasized by the portion of the chirped grating 71 that presently receives the light beam. A coaxial annular region 75 is defined by a sequence of cylindrical sectors 77-$q$ (q=1, 2, . . . , Q; Q≧3) that are spaced apart along a circumference of the annular region 75 by a sequence of axially oriented slots 76-$q$, where slot 76-$q$ separates the two cylindrical sectors, 77-$q$ and 77-$(q+1)$. At least one, and preferably all, of the cylindrical sectors 77-$q$ has an array of one or more light detectors 78-$q$-$p$ (p=1, . . . P; P≧1) thereon that are oriented toward the cylinder z-axis, as illustrated in FIG. 8, to receive some or all of the diffracted light beams 74-$d$. Preferably, the inner surface 79-$q$ of each cylindrical sector 77-$q$ has a light-absorbing material that receives and absorbs a diffracted light beam 74-$d$ that is not received by a light detector 78-$q$-$p$.

The cylindrical structure 73 is optionally rotated around its z-axis, with or without translation of the grating 71 by an amount Δz along this axis. Different photodetector sections 77-$q$ are exposed to different diffracted beams, through chirped diffraction or normal (uniform width) diffraction of the grating, as rotation of the cylindrical structure 73 and/or axial translation of the grating 71 proceed so that different (diffracted) wavelength ranges are presented to light detectors 78-$q$.

The embodiments illustrated in FIGS. 1, 2, 3 and/or 4 can be used to study, and provide time-based and/or wavelength-based correlations of, reactions involving phosphorescence, fluorescence (Stokes shift and anti-Stokes shift), ground state and intermediate state excitation, metastable state de-excitation, other photochemical excitation and decay processes, thermal excitation and relaxation, molecular dissociation, inter-molecular energy transfer, and light absorption in a stationary or flowing fluid, among other processes. These embodiments can also be used to calibrate light emitted in each of one or more wavelength intervals by a light source, against light emitted by a reference light source in each of these wavelength intervals. The embodiment shown in FIG. 4 can be used to analyze and correlate (in time and/or in wavelength) two or more branching or competing photochemical processes, where each process involves a non-overlapping wavelength interval.

Figure 9:
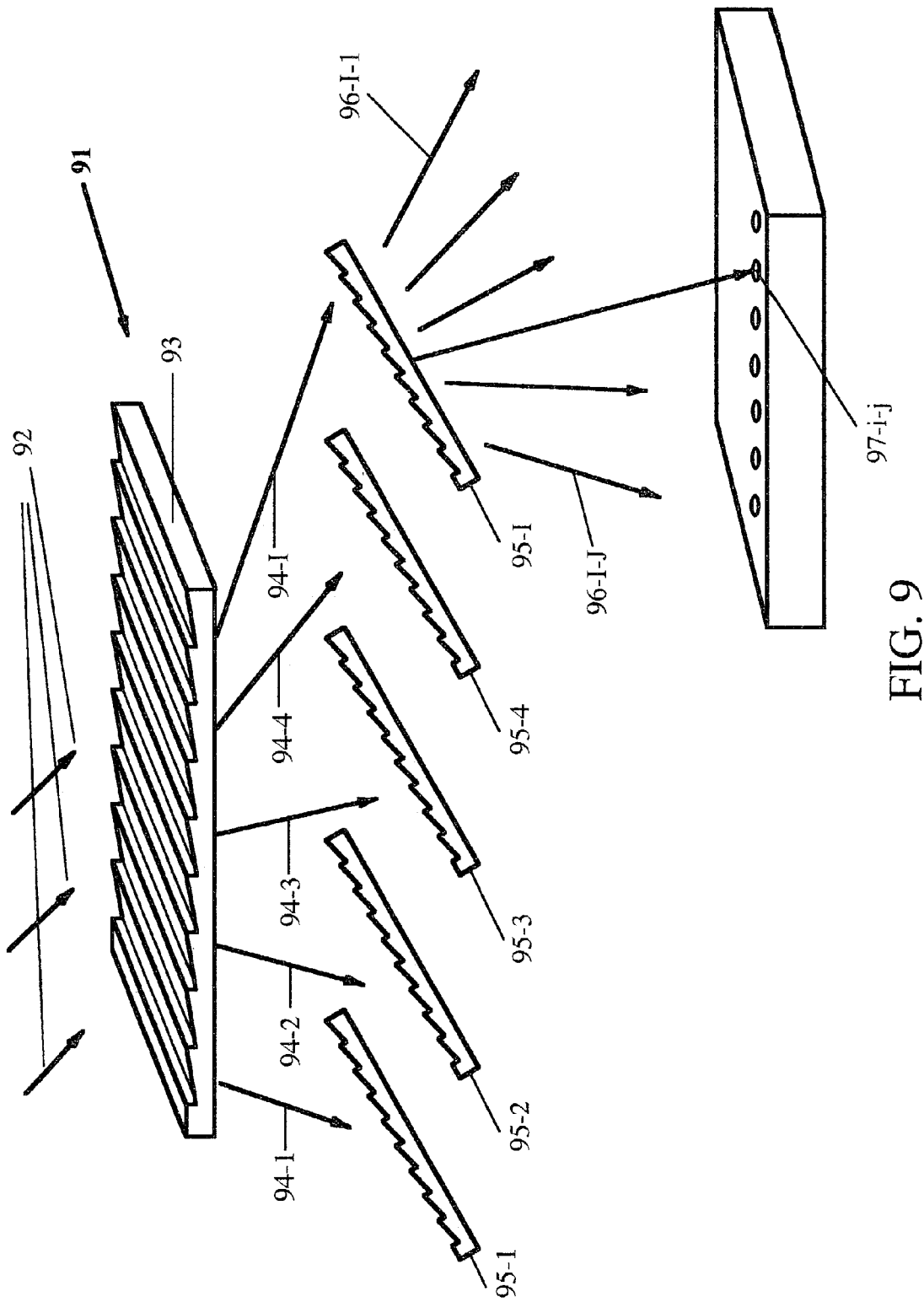

FIG. 9 schematically illustrates another embodiment 91 of the invention, applied to signal coding. A light beam 92 is incident upon a first diffraction grating 93 and is diffracted into several once-diffracted light beams 94-$i$ (i=1, . . . , I; I=5 in FIG. 9). The once-diffracted beam 94-$i$ is received by a diffraction grating 95-$i$, preferably oriented transversely to the orientation of the first grating 93, and is diffracted into a plurality of twice diffracted beams 96-$i$-$j$ (=1, . . . , J (J≧2) so that the total number of twice-diffracted beams 96-$i$-$j$ is I·J (or fewer). Each twice-diffracted beam 96-$i$-$j$ is received by a separate light detector 97-$i$-$j$ that is part of a light detector and processor module 98. The diffraction gratings 93-$i$ need not be oriented parallel to each other and are preferably oriented to capture and further diffract a specified range of wavelengths. Two adjacent wavelength ranges, such as {λ1-i≦λ≦λ2-i} and {λ1-(i+1)≦λ≦λ2-(i+1)} may be overlapping or non-overlapping.

The first diffraction grating 93 preferably has a relatively coarse blazed surface so that each of the once-diffracted beams 94-$i$ includes a relatively large range of wavelengths, λ1-i≦λ≦λ2-i, where each wavelength difference, Δλ(i)=λ2-i−λ1-i, may be 5–100 nm. Each of the diffraction gratings 94-$i$ has a relatively finer blazed surface so that a wavelength range, λ1-(i,j)≦λ≦λ2-(i,j), for the twice-diffracted beam has a much smaller wavelength difference Δ1(i,j)=λ2-(i,j)-λ1-(i,j), of the order of 1–20 nm, or less if desired. Preferably, no two of the twice-diffracted beam wavelength ranges, λ1-(i,j)≦λ≦λ2-(i,j), overlap, except possibly at or near an end of each wavelength interval.

Each light detector element 97-$i$-$j$ receives a portion of the light beam in the wavelength range λ1-(i,j)≦λ≦λ2-(i,j), if light in this wavelength range is included in the incident light beam 92. If each of these wavelength ranges is distinct, the light detector and processor module 98 can distinguish between I·J wavelength ranges that may be present in the incident beam 92, and thus may the incident beam may be associated with as many as $2^{I \cdot J}$ different symbols for coding purposes. Coding applications include encryption/decryption, compression/decompression, error detection/correction, and pseudo-noise symbol generation (e.g., as used in CDMA signals). This maximum number of symbols transmitted, $2^{I \cdot J}$, may be increased further by providing, for each twice-diffracted beam 96-$i$-$j$ issuing from a diffraction grating 95-$i$, a third set of K diffraction gratings (not shown in FIG. 9) that receives the beam 96-$i$-$j$ and diffracts this received beam into K thrice-diffracted beams, thus producing as many as $2^{I \cdot J \cdot K}$ distinct symbols. However, where three diffraction processes are applied seriatim, the wavelength resolution may be less than is desired.

The incident light beam 92 may be received from an optical fiber (not shown in FIG. 9) that includes a temporal sequence of different combinations of "colors" (wavelength ranges), corresponding to a sequence of symbols to be processed and transmitted. The system illustrated in FIG. 9 can function as a two-stage (or more generally Q-stage) wavelength division multiplexer (WDM), in which the first stage and the second stage provide wavelength discrimination for I colors and for I·J colors, as compared to the two-color wavelength discrimination available with a cascaded Mach-Zehnder interferometer system for WDM. An acceptable WDM system must also comply with the flat-top passband response and optical isolation required by the BellCore standards.

What is claimed is:

1. A method for wavelength-based processing of a light beam, the method comprising:
   receiving and diffracting, at a diffraction grating, an incident light beam, produced by at least one of a chemical reaction and a physical reaction at a selected reaction site and having at least first and second apart wavelengths, λ1 and λ2, to provide first and second diffracted beams having the wavelengths λ1 and λ2, respectively;
   receiving the first and second diffracted beams at first and second spaced apart light detectors, respectively;
   determining a time difference between a time said first diffracted beam arrives at said first detector and a time said second diffracted beam arrives at said second detector; and
   characterizing the reaction by a combination of the relative amount of light received by the first and second detectors, the time difference and at least one of the first and second wavelengths.

2. A method for wavelength-based processing of a light beam, the method comprising:
   receiving and diffracting, at a diffraction grating, first and second incident light beams to provide first and second diffracted beams, each beam having first and second wavelength components, from the respective first and second incident light beams;
   receiving the first diffracted beam first and second wavelength components at first and second light detectors at a selected first sequence of light signal sampling times;
   receiving the second diffracted beam first and second wavelength components at third and fourth light detectors at a selected second sequence of light signal sampling times substantially equal to the first sequence of light signal sampling times;
   forming a first correlation value of the first wavelength component for the first and second diffracted beams at the first sequence of light signal sampling times for a first selected time shift value between the first and second diffracted beams first wavelength component;
   forming a second correlation value of the second wavelength component for the first and second diffracted beams at the second sequence of light signal sampling times for a second selected time shift value between the first and second diffracted beams second wavelength component;
   providing a third correlation value that is a non-negative-weighted sum of the first and second correlation values, and comparing the third correlation value with a selected threshold value; and
   when the third correlation value is at least equal to a selected fraction of the threshold value, interpreting this condition as indicating that the first and second incident light beams arise from the same light source.

3. The method of claim 2, further comprising:
   when said third correlation value is less than a second selected fraction of said threshold value, interpreting this condition as indicating that said first and second incident light beams do not arise from said same light source.

4. The method of claim 3, further comprising choosing said second selected fraction to be less than said first selected fraction.

5. The method of claim 3, further comprising choosing said second selected fraction to be equal to said first selected faction.

6. The method of claim 2, further comprising selecting said first time shift value to maximize said first correlation value.

7. The method of claim 2, further comprising selecting said second time shift value to maximize said second correlation value.

8. The method of claim 2, further comprising choosing said second time shift value to be equal to said first time shift value.

9. The method of claim 2, further comprising providing a reference light beam as said first incident light beam.

10. The method of claim 9, further comprising selecting said threshold value to be a weighted sum, over said first and second wavelengths, of a sum of the magnitude squared of an amplitude of said reference light beam signal at each of said first sequence or said second sequence of said light signal sampling times.

11. The method of claim 2, further comprising diffracting said first and second incident light beams using a chirped diffraction grating.

12. A method for wavelength-based processing of a light beam, the method comprising:
receiving and diffracting, at a diffraction grating, first and second, substantially identical, spatially separated incident light beams, and diffracting first and second wavelength components from each of the first and second incident beams to provide first and second wavelength components of the first diffracted beam and first and second wavelength components of the second diffracted beam, from the first and second incident light beams;
passing at least one of the first diffracted beam first wavelength component and the second diffracted beam first, wavelength component through a first chamber having a selected first environment therein;
passing at least one of the first diffracted beam second wavelength component and the second diffracted beam second wavelength component through a second chamber having a selected second environment therein;
receiving the first and second wavelength components of the first diffracted beam and the first and second wavelength components of the second diffracted beam at first, second, third and fourth light detectors, respectively;
comparing at least one selected characteristic of light received at the first and third light detectors, and comparing the at least one selected characteristic of light received at the second and fourth light detectors, to identify at least one characteristic in which the first and second environments differ from each other.

13. The method of claim 12, further comprising choosing, for said characteristic compared for light received at said first and third light detector, a characteristic that indicates amplitude contrast for each of said first wavelength components of said first and second diffracted light beams.

14. The method of claim 12, further comprising choosing, for said characteristic compared for light received at said first and third detector, a characteristic representing concentration of a substance in said first and second chambers.

15. The method of claim 12, further comprising choosing, for said characteristic compared for light received at said first and third light detector, a characteristic that indicates phase contrast for each of said first wavelength components of said first and second diffracted light beams.

16. The method of claim 12, further comprising providing said first environment and said second environment with substantially the same chemical substance, maintained at at least one of (i) distinct first and second temperatures, respectively, and (ii) distinct first and second concentrations, respectively.

17. The method of claim 12, further comprising providing each of said first environment and said second environment with a first chemical substance and a second chemical substance, where concentration of the first chemical substance in said first and second environments is different.

18. The method of claim 17, further comprising providing a different concentration of said second chemical substance in said first and second environments.

19. The method of claim 12, further comprising arranging for said first diffracted beam first wavelength component and said second diffracted beam first wavelength component to have substantially identical optical path lengths in said first environment.

20. The method of claim 19, further comprising arranging for said first diffracted beam second wavelength component and said second diffracted beam second wavelength component to have substantially identical optical path lengths in said second environment.

21. The method of claim 12, further comprising diffracting said first and second incident light beams using a chirped diffraction grating.

22. A method for wavelength-based processing of a light beam, the method comprising:
receiving and diffracting at a diffraction grating first and second incident light beams that may contain selected and spaced apart first and second wavelengths, respectively, and diffracting the first and second incident beams to provide first and second diffracted beams, respectively;
receiving the first and second diffracted beams at a selected reaction site having a reactable substance thereat, and allowing the first and second diffracted beams to react with the substance at first and second times at which the respective first and second diffracted beams arrive at the reaction site;
when interaction of the first and second diffracted beams with the substance produces a specified substance that is physically or chemically transformed from the reactable substance, interpreting this condition as indicating that (i) the first and second incident beams contain the selected first and second wavelengths, respectively and (ii) the second diffracted beam arrives at the reaction site within a selected time interval of the time of arrival of the first diffracted beam at the reaction site.

23. The method of claim 22, further comprising:
when interaction of said first and second diffracted beams with said substance does not produce said specified transformed substance, interpreting this condition as indicating that at least one of the following conditions is not present:
(i) said first and second incident beams contain said selected first and second wavelengths, respectively and (ii) said second diffracted beam arrives at said reaction site within said selected time interval of said time of arrival of said first diffracted beam at said reaction site.

24. The method of claim 22, further comprising:
when interaction of said first and second diffracted beams with said substance does not produce said specified transformed substance, implementing at least one of the following actions: (i) delaying said first time at which said first diffracted beam arrives at said reaction site by a first time delay amount sufficient to allow interaction of the time delayed first diffracted beam and said second diffracted beam to produce said specified transformed substance, and (ii) delaying said second time at which said second diffracted beam arrives at said reaction site by a second time delay amount sufficient to allow interaction of the time delayed second diffracted beam and said first diffracted beam to produce said specified transformed substance.

25. The method of claim 22, further comprising diffracting said first and second incident light beams using a chirped diffraction grating.

26. A method for wavelength-based processing of a light beam, the method comprising:
receiving, at a cylindrically shaped diffraction grating having a cylinder axis and oriented in a first angular position, an incident light beam, and diffracting first and second wavelength components from the incident beam to provide first and second diffracted beams containing the respective first and second wavelength components;

rotating the diffraction grating around the cylinder axis to a second angular position, and receiving and diffracting the incident beam to provide third and fourth diffracted beams containing the respective first and second wavelength components; and providing first, second, third and fourth light detectors, facing and spaced apart from the diffraction grating, to receive the first, second third and fourth diffracted beams, respectively.

27. The method of claim 26, further comprising positioning said light detectors on a sector of a cylinder that is substantially coaxial with said cylindrical axis of said cylindrical diffraction grating.

28. The method of claim 26, further comprising translating said grating in a direction parallel to said cylinder axis, from a first axial position to a second axial position, between a first time interval during which said grating receives and diffracts said incident beam and provides said first and second diffracted beams and a second time interval during which said grating receives and diffracts said incident beam and provides said third and fourth diffracted beams.

29. The method of claim 26, further comprising providing said diffraction grating as a chirped grating.

30. A method for wavelength-based processing of a light beam, the method comprising:

receiving and diffracting at a first diffraction grating, numbered 0, an incident light beam to provide I once-diffracted beams b(i), numbered i=1, ... ,I, with I≧2, where the beam b(i) contains light, if any, in a selected wavelength range, $\lambda1(i) \leq \lambda \leq \lambda2(i)$;

receiving and diffracting at least two once-diffracted beams, b(i) and b(i'), at diffraction gratings, numbered i and i', respectively, with $1 \leq i < i' \leq I$, to provide J twice-diffracted beams, denoted b(i,j), and J twice-diffracted beams, denoted b(i',j'), with j=1, ... , J and j'=1, ... , J and J≧2, where the beam b(i,j) contains light, if any, in a selected wavelength range, $\lambda1(i,j) \leq \lambda \leq \lambda2(i,j)$ and the beam b(i',j') contains light, if any, in a selected wavelength range, $\lambda1(i',j') \leq \lambda \leq \lambda2$ (ii',j');

positioning first and second light detectors, denoted d(i,j) and d(i',j'), to receive light that is present in the twice-diffracted beam b(i,j) at the first light detector and to receive light that is present in the beam b(i',j') at the second light detector; and when light is received at the first and second light detectors, d(i,j) and d(i',j'), interpreting this condition as indicating that light in the wavelength range $\lambda1(i,j) \leq \lambda \leq \lambda2(i,j)$ and in the wavelength range $\lambda1(i',j') \leq \lambda \leq \lambda2(i',j')$ is present in the incident light beam.

31. The method of claim 30, further comprising: (1) indicating presence of one or more of a selected group of symbols in a signal by including in said incident light beam light in said wavelength range $\lambda1(i,j) \leq \lambda \leq \lambda2(i,j)$ and light in said wavelength range $\lambda1(i',j') \leq \lambda \leq \lambda2(i',j')$.

32. The method of claim 30, further comprising:

when light is received at said first light detector d(i,j) and is not received at said second light detector d(i',j'), interpreting this condition as indicating that light in the wavelength range $\lambda1(i,j) \leq \lambda \leq \lambda2(i,j)$ is present in said incident light beam and light in the wavelength range $\lambda1(i',j') \leq \lambda \leq \lambda2(i',j')$ is not present in said incident light beam.

33. The method of claim 32, further comprising: (1) indicating presence of one or more of a selected group of symbols in a signal by including in said incident light beam light in said wavelength range $\lambda1(i,j) \leq \lambda \leq \lambda2(i,j)$ and not including light in said wavelength range $\lambda1(i',j') \leq \lambda \leq \lambda2(i',j')$.

34. The method of claim 30, further comprising:

when light is not received at said first light detector d(i,j) and is not received at said second light detector d(i',j'), interpreting this condition as indicating that light in the wavelength range $\lambda1(i,j) \leq \lambda \leq \lambda2(i,j)$ is not present in said incident light beam and light in the wavelength range $\lambda1(i',j') \leq \lambda \leq \lambda2(i',j')$ is not present in said incident light beam.

35. The method of claim 34, further comprising: (1) indicating presence of one or more of a selected group of symbols in a signal by not including in said incident light beam light in said wavelength range $\lambda1(i,j) \leq \lambda \leq \lambda2(i,j)$ and not including light in said wavelength range $\lambda1(i',j') \leq \lambda \leq \lambda2(i',j')$.

36. A system for wavelength-based processing of a light beam, the system comprising:

a diffraction grating, positioned to receive and diffract an incident light beam, produced by at least one of a chemical reaction and a physical reaction at a selected reaction site and having at least first and second distinct wavelengths, λ1 and λ2, to provide first and second diffracted beams having the wavelengths λ1 and λ2, respectively;

first and second, spaced apart light detectors, positioned to receive the first and second diffracted beams at first and second spaced apart light detectors, respectively; and a computing device programmed:
to receive signals from the first and second light detectors and to characterize the reaction by the relative amount of light received by the first and second light detectors;
to determine a time difference between a time the first diffracted beam arrives at the first detector and a time the second diffracted beam arrives at the second detector; and
to further characterize the reaction by the time difference and by at least one of the first and second wavelengths.

37. A system for wavelength-based processing of a light beam, the system comprising:

a diffraction grating, positioned to receive and diffract first and second incident light beams to provide first and second diffracted beams, each beam having first and second wavelength components, from the respective first and second incident light beams;

a light detector mechanism having;
first and second light detectors to receive the first diffracted beam first and second wavelength components, respectively, at a first selected sequence of light signal sampling times; and
third and fourth light detectors to receive the second diffracted beam first and second wavelength components, respectively, at a second selected sequence of light signal sampling times substantially equal to the first sequence of light signal sampling times;

a computing device programmed:
to form a first correlation value of the first wavelength component for the first and second diffracted beams at the first sequence of light signal sampling times for a first selected time shift value between the first and second diffracted beams first wavelength component;
to form a second correlation value of the second wavelength component for the first and second diffracted beams at the second sequence of light signal sampling times for a second selected time shift value between the first and second diffracted beams second wavelength component;

to provide a third correlation value that is a non-negative-weighted sum of the first and second correlation values, and comparing the third correlation value with a selected threshold value; and when the third correlation value is at least equal to a selected fraction of the threshold value, to interpret this condition as indicating that the first and second incident light beams arise from the same light source.

38. The system of claim 37, wherein said computing device is further programmed so that:

when said third correlation value is less than a second selected fraction of said threshold value, to interpret this condition as indicating that said first and second incident light beams do not arise from said same light source.

39. A system for wavelength-based processing of a light beam, the system comprising:

a diffraction grating, positioned to receive and diffract first and second, substantially identical, spatially separated incident light beams, and diffracting first and second wavelength components from each of the first and second incident beams to provide first and second wavelength components of the first diffracted beam and first and second wavelength components of the second diffracted beam, from the first and second incident light beams;

a first chamber, having a selected first environment therein, that receives and allows at least one of the first diffracted beam first wavelength component and the second diffracted beam first wavelength component to pass through the first chamber;

a second chamber, having a selected second environment therein, that receives and allows at least one of the first diffracted beam second wavelength component and the second diffracted beam second wavelength component to pass through the second chamber;

first, second, third and fourth spaced apart light detectors, positioned to receive the first and second wavelength components of the first diffracted beam and the first and second wavelength components of the second diffracted beam at first, second, third and fourth light detectors, respectively; and a computing device that is programmed to receive signals from the first, second, third and fourth light detectors, to compare at least one selected characteristic of light received at the first and third light detectors, to compare the at least one selected characteristic of light received at the second and fourth light detectors, and to identify at least one characteristic in which the first and second environments differ from each other.

40. The system of claim 39, wherein said characteristic compared for light received at said first and third light detector, is selected to be a characteristic that indicates at least one of amplitude contrast and phase contrast for each of said first wavelength components of said first and second diffracted light beams.

41. The system of claim 39, wherein said first environment and said second environment are provided with substantially the same chemical substance that is maintained at at least one of (i) distinct first and second temperatures, respectively, and (ii) distinct first and second concentrations, respectively.

42. The system of claim 39, wherein each of said first environment and said second environment is provided with a first chemical substance and a second chemical substance, where concentration of the first chemical substance in said first and second environments is different.

43. A system for wavelength-based processing of a light beam, the system comprising:

a diffraction grating, positioned to receive and diffract first and second incident light beams that may contain selected and spaced apart first and second wavelengths, respectively, and to diffract the first and second incident beams to provide first and second diffracted beams, respectively;

a reaction site having a reactable substance, that receives the first and second diffracted beams and allows the first and second diffracted beams to react with the substance at first and second times at which the respective first and second diffracted beams arrive at the reaction site; and a computing device programmed:

when interaction of the first and second diffracted beams with the substance produces a specified substance that is physically or chemically transformed from the reactable substance, to interpret this condition as indicating that (i) the first and second incident beams contain the selected first and second wavelengths, respectively and (ii) the second diffracted beam arrives at the reaction site within a selected time interval of the time of arrival of the first diffracted beam at the reaction site.

44. The system of claim 43, wherein said computing device is programmed:

when interaction of said first and second diffracted beams with said substance does not produce said specified transformed substance, to interpret this condition as indicating that at least one of the following conditions is not present: (i) said first and second incident beams contain said selected first and second wavelengths, respectively and (ii) said second diffracted beam arrives at said reaction site within said selected time interval of said time of arrival of said first diffracted beam at said reaction site.

45. A system for wavelength-based processing of a light beam, the system comprising:

a cylindrically shaped diffraction grating having a cylinder axis and oriented in a first angular position, positioned to receive an incident light beam and to diffract first and second wavelength components from the incident beam to provide first and second diffracted beams containing the respective first and second wavelength components;

rotation means to rotate the diffraction grating around the cylinder axis to a second angular position so that the incident beam is received and diffracted to provide third and fourth diffracted beams containing the respective first and second wavelength components; and first, second, third and fourth light detectors, facing and spaced apart from the diffraction grating, positioned to receive the first, second third and fourth diffracted beams.

46. The system of claim 45, further comprising translation means to translate said grating in a direction parallel to said cylinder axis, from a first axial position to a second axial position, between a first time interval during which said grating receives and diffracts said incident beam and provides said first and second diffracted beams and a second time interval during which said grating receives and diffracts said incident beam and provides said third and fourth diffracted beams.

47. A system for wavelength-based processing of a light beam, the system comprising:
- a first diffraction grating, numbered 0, positioned to receive and diffract an incident light beam to provide I once-diffracted beams b(i), numbered i=1, . . . , I, with I≧2, where the beam b(i) contains light, if any, in a selected wavelength range, $\lambda 1(i) \leq \lambda \leq \lambda 2(i)$;
- a sequence of at least two diffraction gratings, numbered i and i' with 1≦i<i'≦I, positioned to receive and diffract the once-diffracted beams, b(i) and b(i'), to provide J twice diffracted beams, denoted b(i,j), and J twice-diffracted beams, denoted b(i',j'), with j=1, . . . , J and j'=1, . . . , J and J≧2, where the beam b(i,j) contains light, if any, in a selected wavelength range, $\lambda 1(i,j) \leq \lambda \leq \lambda 2(i,j)$ and the beam b(i',j') contains light, if any, in a selected wavelength range, $\lambda 1(i',j') \leq \lambda \leq \lambda 2(ii',j')$;
- first and second light detectors, denoted d(i,j) and d(i',j'), positioned to receive light that is present in the twice-diffracted beam b(i,j) at the first light detector, and to receive light that is present in the beam b(i',j') at the second light detector; and
- a computing device programmed so that, when light is received at the first and second light detectors, d(i,j) and d(i',j'), to interpret this condition as indicating that light in the wavelength range $\lambda 1(i,j) \leq \lambda \leq \lambda 2(i,j)$ and in the wavelength range $\lambda 1(i,j) \leq \lambda \leq \lambda 2(i',j')$ is present in the incident light beam.

48. The system of claim 47, wherein said computing device is further programmed to indicate presence of one or more of a selected group of symbols in a signal by including in said incident light beam light in said wavelength range $\lambda 1(i,j) \leq \lambda \leq \lambda 2(i,j)$ and light in said wavelength range $\lambda 1(i',j') \leq \lambda \leq \lambda 2(i',j')$.

49. The system of claim 47, wherein said computing device is further programmed to indicate presence of one or more of a selected group of symbols in a signal by including in said incident light beam light in said wavelength range $\lambda 1(i,j) \leq \lambda \leq \lambda 2(i,j)$ and not including light in said wavelength range $\lambda 1(i',j') \leq \lambda \leq \lambda 2(i',j')$.

50. The system of claim 47, wherein said computing device is further programmed to indicate presence of one or more of a selected group of symbols in a signal by not including in said incident light beam light in said wavelength range $\lambda 1(i,j) \leq \lambda \leq \lambda 2(i,j)$ and not including light in said wavelength range $\lambda 1(i',j') \leq \lambda \leq \lambda 2(i',j')$.

* * * * *